United States Patent [19]

Manning et al.

[11] 4,349,352
[45] Sep. 14, 1982

[54] TEST FOR GLUCOSYLATED HEMOGLOBIN AND OTHER GLUCOSYLATED PROTEINS

[75] Inventors: James M. Manning, Tenafly; Seetharama A. Acharya, Cresskill, both of N.J.

[73] Assignee: Rockefeller University, New York, N.Y.

[21] Appl. No.: 178,068

[22] Filed: Aug. 14, 1980

[51] Int. Cl.³ .................... G01N 33/68; G01N 33/72
[52] U.S. Cl. .................................. 23/230 B; 23/901; 23/913
[58] Field of Search .................... 23/230 B, 901, 913; 252/408; 422/61

[56] References Cited

U.S. PATENT DOCUMENTS 4,142,855 3/1979 Acuff ............................... 422/68 X
4,268,270 5/1981 Gabbay et al. .................. 23/901 X

OTHER PUBLICATIONS

Shriner et al., "The Systematic Identification of Organic Compounds", John Wiley & Sons, Inc., New York, 3rd Edition, 1948, pp. 116–117, A.U. 173.
Grammaticakis, Chemical Abstracts, vol. 46, 1952, No. 46:11133f.

Primary Examiner—Arnold Turk
Attorney, Agent, or Firm—E. Janet Berry

[57] ABSTRACT

The invention is a process for a rapid and precise colorimetric method for determination of the total glucosylated blood proteins. The method is especially adapted and useful as a clinical, diagnostic aid for identification, management and treatment for diabetics. The method essentially comprises use of phenylhydrazine derivatives as reagents to determine the extent of glucosylation of hemoglobin and other proteins in the blood samples tested. The adduct of the aldehyde sugar (glucose) and the hemoglobin possesses the ketoamine structure. This structure is readily detected colorimetrically after treatment with a phenylhydrazine to give the corresponding phenylhydrazone. Phenylhydrazine and 2,4-dinitrophenylhydrazine are preferred reagents for the diagnostic process.

8 Claims, 3 Drawing Figures

TEST FOR GLUCOSYLATED HEMOGLOBIN AND OTHER GLUCOSYLATED PROTEINS

The research leading to this invention was supported by National Institutes of Health grant-HL 18819. The U.S. Government has certain rights in this invention.

The invention pertains generally to a novel, rapid, and very precise method for determination of total glucosylated blood proteins. The method is especially useful as a diagnostic aid for diabetics. The total of glucosylated blood proteins includes $HbA_{1a}$, $AbA_{1b}$, and $HbA_{1c}$ all of which constitute HbA. The production of glucosylated hemoglobin ($HbA_{1c}$) is a direct function of the total free glucose and is therefore elevated in diabetics.

At present it is possible to determine accurately glucosylated hemoglobins by column chromatography. Since the $HbA_{1c}$ level reflects the total of glucosylated proteins produced over a period of 4 to 6 weeks, it serves as a measure of the average serum glucose level over that period of time. However, at least two disadvantages of this technique are (1) the amount of time required for the analysis and (2) the fact that the amount of glucose bound to the major hemoglobin fraction, $HbA_0$, and to serum albumin, are not measured by this method. More recently, a process of high performance liquid chromatography has been used to determine $HbA_{1c}$, thus shortening the analysis time. An alternative technique for determination of glucosylated hemogoblin is use of thiobarbituric acid for estimation of the amounts of hydroxymethylfurfural formed during heating of the glucosylated hemoglobin under acidic conditions. The results obtained with this procedure have been satisfactory and fair correlation with the chromatographic method is found. However, one disadvantage of this method is requirement for a heating step at 100° for a substantial period of time. Another technique based on radioimmunoassay has also been reported but it is not yet in wide use. Thus, a need exists for a precise procedure which could be automated for more rapid analysis. In addition, it is regarded as desirable to have available a method to measure the total amounts of glucosylated proteins in blood in order to give a more complete picture of the extent of glucosylated protein in vivo as a diagnostic tool.

Recent studies have helped to elucidate the chemistry of the reaction between hemoglobin and the 3-carbon sugar aldehyde, glyceraldehyde. It has recently been discovered that the Schiff base formed between hemoglobin and glyceraldehyde is limited to 5 of the possible 24 amino groups per $\alpha\beta$ dimer of hemoglobin. These residues are more specifically lys-16 ($\alpha$), lys-82 ($\beta$), lys-59 ($\beta$), lys-120 ($\beta$), and val-1 ($\beta$). The latter residue is the one which is glucosylated in $HbA_{1c}$ and results in chromatographic separation of this component from the major hamoglobin fraction, $HbA_o$. However, the $HbA_o$ fraction contains some glucosylated lysine residues and some of these are the same residues which react with glyceraldehyde. The comparative chemistry of the reactions of these two sugars with Hb is of current interest and is currently under study.

Figure 2:
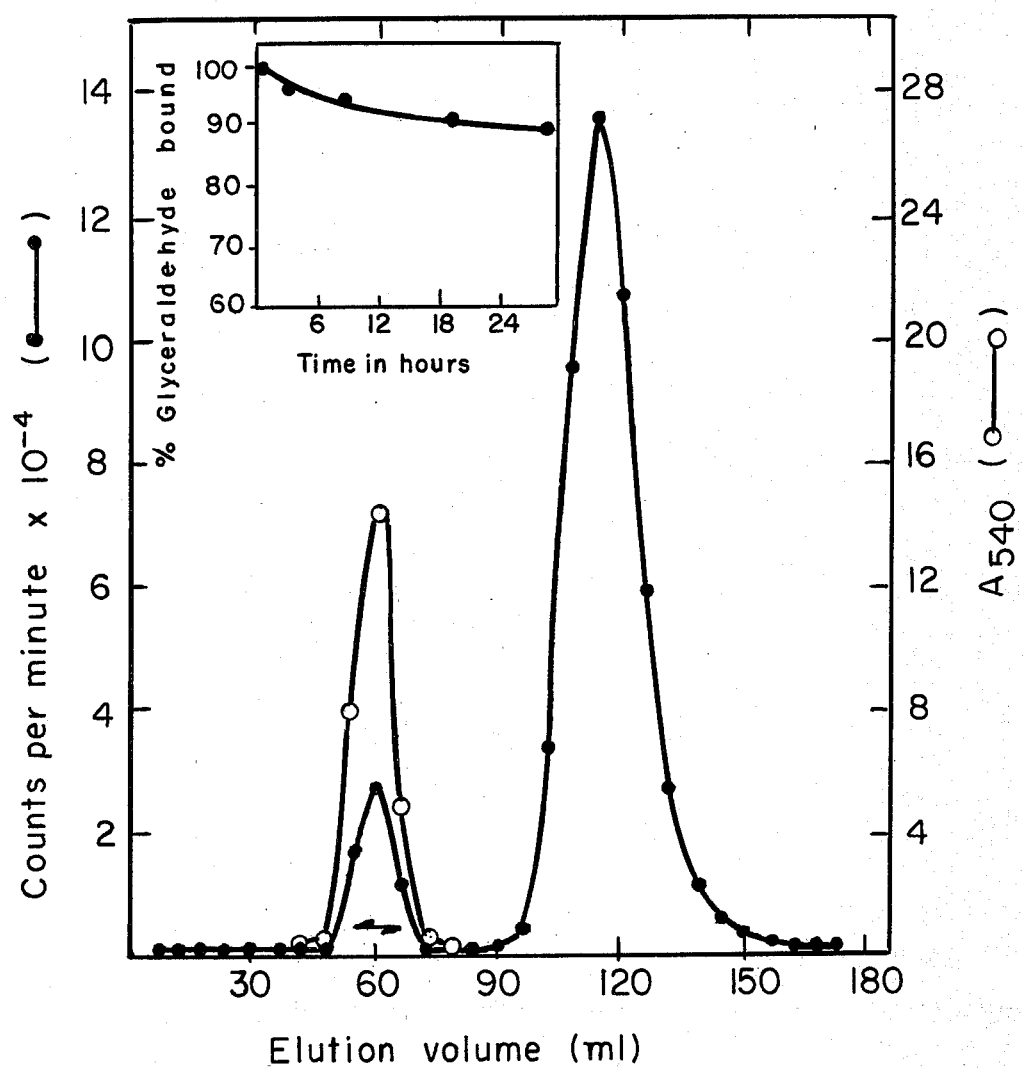
FIG. 2 shows the elution of a radioactively-tagged glyceraldehyde-treated HbA through a column bed.

The inset in FIG. 2 shows the release of radioactively-tagged glyceraldehyde from hemoglobin-glyceraldehyde adduct.

Figure 3:
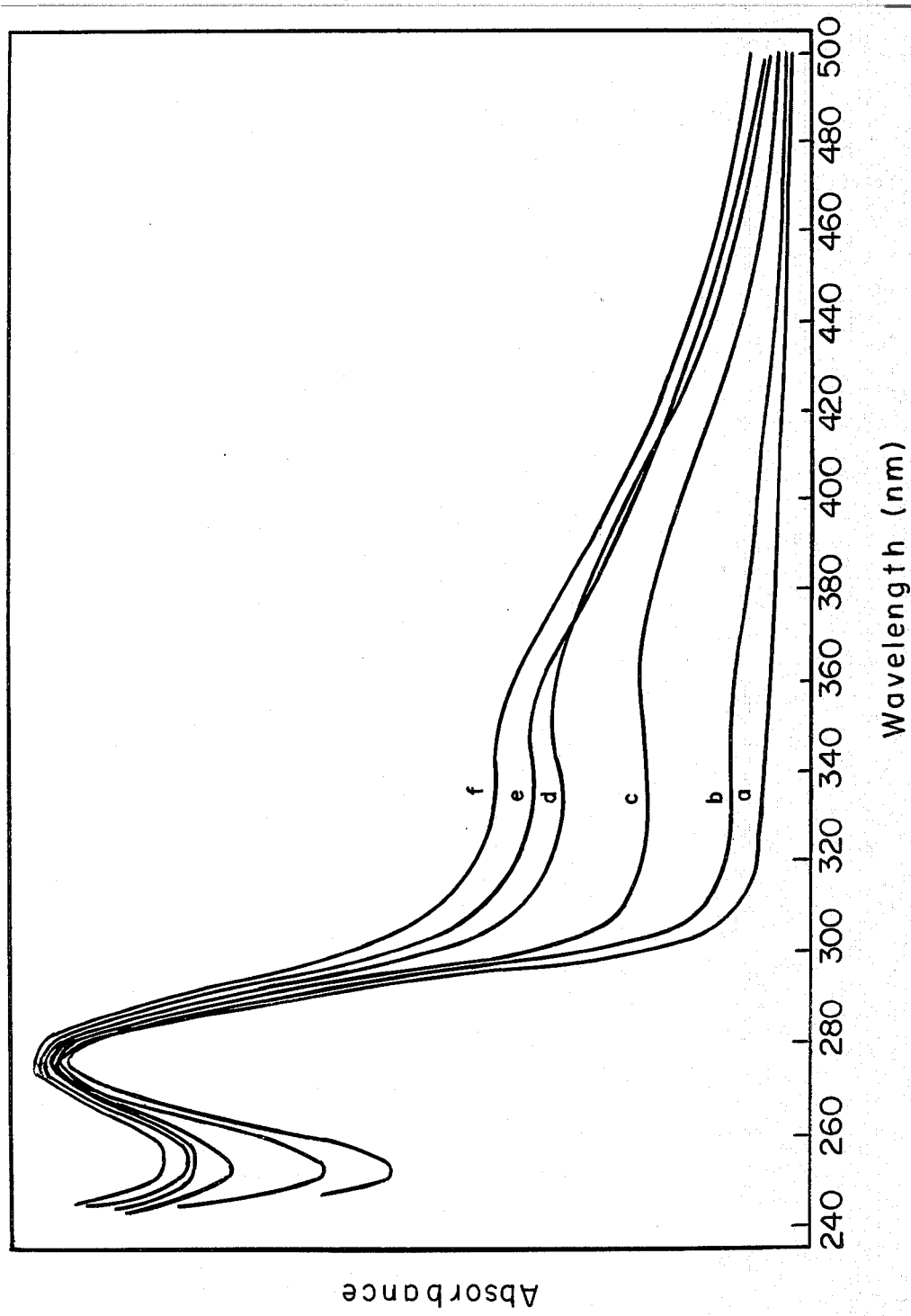

FIG. 3 is a plot of the absorption spectra of the phenylhydrazone of glycosylated hemoglobin-phenylhydrazine adduct. The curves a to f shown thereon represent increasing concentrations of glyceraldehyde/mole of HbA.

Figure 1:
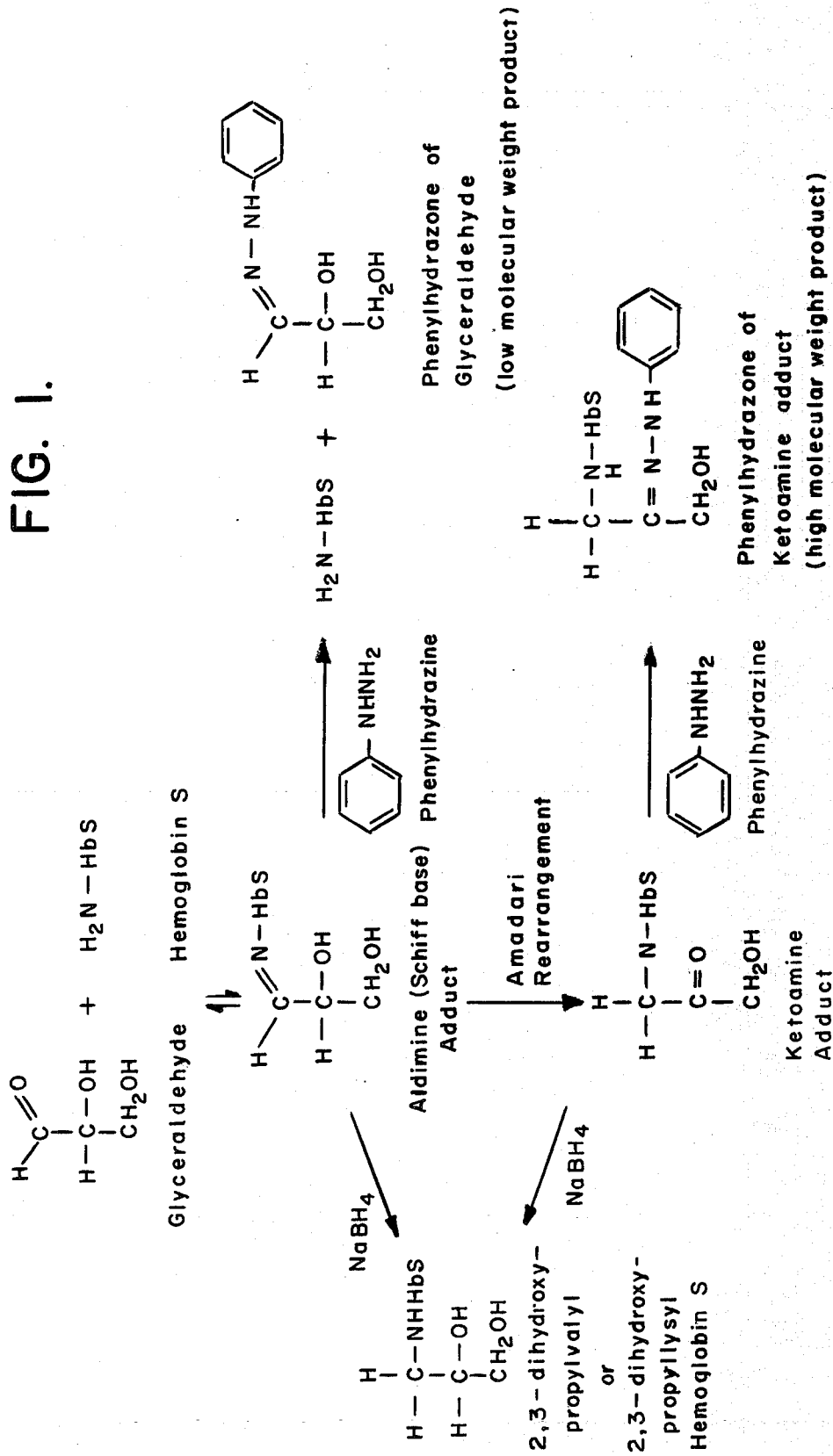
FIG. 1 is a schematic representation of the reaction of phenylhydrazine with the carbonyl function of the ketomine linkage of glyceraldehyde with HbA. This figure describes the basic chemistry involved in the development of the assay of the invention showing the reactivity of the carbonyl function of the ketoamine linkage toward hydrazines.

It has now been found that the compound, phenylhydrazine can readily be used to distinguish between aldimine or ketoamine linkages of glyceraldehyde to hemoglobin (Hb). FIG. 1 shows the reaction scheme of the glyceraldehydephenylhydrazine reaction. With the glyceraldehyde-Hb adduct, the phenylhydrazone formation is rapid and takes place under relatively mild conditions. Experimental work has shown that all of the glyceraldehyde present in a stable ketoamine linkage (FIG. 2) is of the same type as that present in $HbA_{1c}$. Thus, the correlation of the amounts of glucosylated hemoglobin and particularly $HbA_{1c}$ (wherein glucose is linked to val-1 ($\beta$) as a ketoamine) with increased concentrations of circulating glucose in the diabetic is the basis for monitoring the diabetic condition.

The glucosylated hemoglobin-phenylhydrazine adduct product is then measured by the determination of the absorbance at 350–450 nm of the yellow chromophore due to the phenylhydrazone (after removal of heme from protein) (FIG. 3). In FIG. 3, the curves identified as a,b,c,d,e, and f are the absorbance curves of the yellow chromophore due to the phenylhydrazone in samples of the glucosylated hemoglobin-phenylhydrazine adduct product. Thus there has been discovered and developed a simple, quantitative method adaptable for clinical use whereby non-enzymic glucosylated blood proteins can be measured. The method is based on the fact that the adduct of glyceraldehyde and hemoglobin possesses the ketoamine structure and that this can readily be detected on the protein after treatment with a phenylhydrazine to produce a phenylhydrazone. The presence of ketoamine moities on glucosylated hemoglobins, such as hemoglobin $A_{1c}$, can be directly demonstrated by simple colorimetric tests.

The reaction of phenylhydrazine, 2,4-dinitrophenylhydrazine and other such phenylhydrazine reagents with total blood proteins with the aim of developing a quantitative measure of the amount of ketoamine adducts of glucose attached to these proteins.

Fluorescent hydrazine reagents, such as dansylhydrazine, are also considered to be especially useful for forming the hydrazone derivatives, as they facilitate and increase usefulness and accuracy of the tests which are carried out for measurements and evaluation.

It is possible to carry out the steps which comprise the invention by coordinating them in an automated procedure, whereby there is provided both more efficient and more rapid procedures for obtaining routine clinical data.

It is also possible to use the methods and techniques of this invention to identify and measure glucosylated proteins other than blood proteins.

The invention will be further illustrated and detailed by the Examples set forth below but it is in no way intended to limit specifically the invention thereto.

EXAMPLE 1

If desired, as protein precipitant, acid-acetone, of the classical method, can be employed. However, ethanol can be used in place of acetone to precipitate blood proteins in the blood sample. It is preferred also that chloroform be included in the precipitation mixture to facilitate removal of the heme. A quantity of 4 ml of a mixture of $C_2H_5OH/CHCl_3/HCl$ (50/48/2) when mixed with 0.5 ml of heparinized whole blood from normal human volunteers gives satisfactory precipitation of the protein and solubilization of the heme. After centrifugation of the resulting mixture in a clinical centrifuge, the brown supernatant liquid is removed by aspiration. The precipitate recovered is mixed well on a Vortex mixer with 4 ml more of the precipitant solution. Four such treatments give a pure-white protein precipitate in about 10 min.

In order to determine the amount of ketoamine adduct produced in the purified protein sample, the treatment with phenylhydrazine is carried out at a pH of about 5. It is preferred to carry out preliminary washing of the precipitate with absolute ethanol to remove residual chloroform. If this is not done, a two phase system may form and complicate the absorbance readings. The subsequent step of the procedure for forming the adduct with the phenylhydrazine in sodium acetate is carried out at a pH of about 5. Using phenylhydrazine itself, the yellow adduct is formed in 15 min. at 37°. The final absorbance reading is conveniently obtained on this reaction mixture. In order to do so, it is important to keep the protein as concentrated as possible in about a 1 ml of the phenylhydrazine solution. This makes it possible to obtain significant absorbance at $A_{350}$ when the reading is obtained against a reagent blank. If the reagent blanks are too high then it is necessary to precipitate the phenylhydrazone-protein derivative, wash it free of unreacted phenylhydrazine with 95% ethanol and redissolve it in acetic acid which is a very good solvent for globin.

This procedure needs no other modifications in order to make it adaptable and totally acceptable for clinical use. Only routine adjustments for sensitivity of the proposed assay may be required.

EXAMPLE 2

The sensitivity of the method is readily estimated by assuming that the molar extinction coefficient of 7500 calculated for the glyceraldehyde-Hb phenylhydrazone adduct is applicable to the glucose-Hb adduct. Thus, starting with 0.5 ml of whole blood at a normal hematocrit, about 0.5 mole of Hb would be used. If recovery at the precipitation stage(s) is about 100%, and if the protein phenylhydrazone is dissolved in 1 ml of acetic acid then the Hb concentration is 0.5 mM. If about 5% of the Hb (from normal individuals) is present as $HbA_{1c}$ then the concentration of this $HbA_{1c}$ would be 0.025 mM. An absorbance reading of 0.19 for this phenylhydrazone would be expected. In diabetics, however, with 10% $HbA_{1c}$, an absorbance of 0.38 would be found. In fact, an even higher reading may well be obtained especially if the ketoamine adduct on $HbA_o$ (on the lysine residues) and on serum albumin also contribute to the absorbance of the phenylhydrazone derivatives. Such a possibility is discussed in greater detail hereinbelow.

EXAMPLE 3

The 2,4-dinitro derivative of phenylhydrazine is the preferred reagent for the identification of organic carbonyl compounds. In general, its application to protein carbonyl functions is carried out under strongly acidic conditions. The great advantage of this substituted phenylhydrazine as reagent is relatively high extinction coefficient of the derivative in the 370–400 nm range. In addition, solutions of this reagent are more stable than are solutions of phenylhydrazine and therefore this reagent is believed more desirable for purposes of automation.

The formation of 2,4-dinitrophenylhydrazones of carbonyl compounds is conveniently accomplished in 2NHCl in which the reagent is soluble. However, such acidic conditions are incompatible with globin which is insoluble under strongly acidic conditions. Thus, it is preferred to carry out the reaction of this reagent with globin (precipitated and prepared as described above) in 15% acetic acid in which globin is very soluble. It is sometimes necessary to increase the acidity of the medium somewhat by including small amounts of phosphoric acid.

EXAMPLE 4

The protein $HbA_{1c}$ is prepared by known chromatographic and isoelectric focusing methods. The chemical structure of this minor hemoglobin is known in detail. It is quite possible and practical to use it as a standard to calculate the extinction coefficient of the phenylhydrazone and the dinitrophenylhydrazone of the products prepared as described in the above examples. The globin is first prepared by treatment of the hemoglobin with the $C_2H_5OH/CHCl_3/HCl$ mixture described above. As a blank, the $HbA_{1c}$ is treated with $NaBH_4$, which reduces the ketoamine and renders it unreactive with the phenylhydrazine reagent. The reduced protein is then mixed with the same phenylhydrazine reagent as the unreduced protein and used as an absorbance blank.

Thus samples $HbA_{1c}$ from both normal and from diabetic individuals are obtained and compared as background data. The results obtained with the phenylhydrazine assays can then be compared with the chromatographic analysis obtained on the same samples. In this way, the accuracy and reproducibility of the tests can be determined.

EXAMPLE 5

As a final step in the diagnostic method, the phenylhydrazone and/or the 2,4-dinitrophenylhydrazone derivatives of the hemoglobins (or of serum albumin) as prepared above are scanned for absorbance in the 260–500 nm region. The protein concentration is estimated from the 280 nm reading. The peak absorbance for the hydrazone derivatives is determined. The scans are repeated at selected time intervals in order to determine rate of formation and the stability of the chromophore. At the optimal time for color development, the ratio of hydrazone absorbance to protein absorbance comprises the measure of aldimine or ketoamine adduct present. Thus, any differences in the initial amounts of blood samples taken for analysis do not affect the results, since the ratio of absorbance values are invarient with sample size. The reagent blank is the protein sample treated with $NaBH_4$ prior to the addition of phenylhydrazine or 2,4-dinitrophenylhydrazine.

The effect of pH on the amount and position of the absorbance peaks of each protein derivative may cause some slight but constant variations. These derivatives can be stabilized and thus higher absorbance at higher pH values, although their formation is facilitated in acidic solution. In these tests, the limitations can be solubility at certain selected pH values.

The stability of the adducts at 37° as a function of time at neutral pH is satisfactory. In the event hydrolysis takes place, however, the absorbance from the phenylhydrazone changes somewhat. Thus analyses can be performed if desired for each of the protein derivatives separately and for the total blood proteins under similar conditions and time. These results may well have some bearing on the interpretation of data from future clinical studies on the same patients.

What is claimed is:

1. A method for identification and assay of glucosylated blood proteins which comprises the steps of isolating purified glucosylated blood protein, treating said isolated protein with a phenylhydrazine adapted to react therewith, and thereafter measuring the absorption coefficient of the resulting phenylhydrazone.

2. The method of claim 1 in which the phenylhydrazine is phenylhydrazine.

3. The method of claim 1 in which the phenylhydrazine is 2,4-dinitrophenylhydrazine.

4. The method of claim 1 in which the absorption coefficient of the phenylhydrazone is measured as an extinction coefficient in the 350–450 nm range.

5. The method of claim 1 in which the absorption coefficient is measured and compared with a standard value, thereby quantitatively determining the amount of glucose present in the glucosylated blood proteins starting materials.

6. The method of claim 1 in which the starting material is human blood hemoglobin.

7. The method of claim 1 in which the glucosylated blood proteins measured is essentially $HbA_{1c}$.

8. The method of claim 1 wherein the step of isolating includes precipitation of the glucosylated blood protein, centrifugation of the precipitated mixture and aspiration of the supernatant liquid leaving a purified protein sample.

* * * * *